United States Patent [19]
Suzuki et al.

[11] Patent Number: 5,219,999
[45] Date of Patent: Jun. 15, 1993

[54] IMMUNOGLOBULIN G AND PROCESS FOR THE PRODUCTION THEREOF

[75] Inventors: Tohru Suzuki; Hiroyuki Ikeda, both of Tokyo; Kazuyo Ikeda, Urawa; Tsugikazu Tomono, Kashiwa; Sadayoshi Sekiguchi, Sapporo; Takeji Ohtani, Tokyo; Seigi Suzuki, Aichi, all of Japan

[73] Assignees: Mitsubishi Rayon Co., Ltd.; The Japanese Red Cross Society, both of Tokyo, Japan

[21] Appl. No.: 669,992

[22] Filed: Mar. 15, 1991

[30] Foreign Application Priority Data

Mar. 20, 1990 [JP] Japan ................... 2-68210

[51] Int. Cl.$^5$ .................. C07K 3/12; C07K 3/26
[52] U.S. Cl. .................. 530/390.5; 530/414; 530/417; 530/427
[58] Field of Search .......... 530/387, 412, 414, 417, 530/390.5, 427; 424/85.8

[56] References Cited

U.S. PATENT DOCUMENTS

| | | | |
|---|---|---|---|
| 3,743,480 | 7/1973 | Falk | 530/427 |
| 4,333,870 | 6/1982 | Koyama et al. | 530/390.5 |
| 4,708,799 | 11/1987 | Gerlach et al. | 210/500.23 |
| 4,933,092 | 6/1990 | Aunet et al. | 210/729 |
| 5,022,988 | 6/1991 | Okarma et al. | 436/178 |

FOREIGN PATENT DOCUMENTS

| | | |
|---|---|---|
| 0085747 | 8/1983 | European Pat. Off. |
| 0246579 | 11/1987 | European Pat. Off. |
| 0268973 | 6/1988 | European Pat. Off. |
| 0270025 | 6/1988 | European Pat. Off. |
| 2026076 | 5/1979 | Fed. Rep. of Germany |
| WO86/06727 | 11/1986 | PCT Int'l Appl. |

OTHER PUBLICATIONS

Patent Abstracts of Japan, vol. 10, No. 235, Aug. 14, 1986, & JP-A-61-69 732, Apr. 10, 1986, H. Takeda, et al., "Immunogloblin Preparation for Intravenous Injection".
Database WPIL, No. 82-14904E, & JP-A-57 009 723, Jan. 19, 1982.
Wang et al., J. Parent. Sci. Tech., Supplement vol. 42 No. 25 pp. 53-524 (1988).
Agishi, Membrane, vol. 7(2), pp. 95-104 (1982).
Arenkov et al., Ulcr. Biolchim. Zh., vol. 61(6) pp. 89-92 (1989).

Primary Examiner—Jeffrey E. Russel
Attorney, Agent, or Firm—Oblon, Spivak, McClelland, Maier & Neustadt

[57] ABSTRACT

Crude immunoglobulin G isolated from human blood plasma is treated according to a conventional technique (such as the tricalcium phosphate adsorption method) to remove aggregates therefrom to such an extent that they are not detectable by gel filtration analysis. In order to produce an aqueous solution of immunoglobulin G having a reduced anticomplementary activity, the resulting solution is then filtered through a porous polyolefin membrane having a pore size larger than the molecular size of immunoglobulin G, in the presence of a stabilizer having surface activity. The aqueous solution of immunoglobulin G so produced is suitable for use in intravenous injection because its anticomplementary activity is low.

9 Claims, 1 Drawing Sheet

IMMUNOGLOBULIN G AND PROCESS FOR THE PRODUCTION THEREOF

BACKGROUND OF THE INVENTION

1. Field of the Invention

This invention relates to a process for the production of an immunoglobulin G preparation having low anticomplementary activity and suitable for use in intravenous injection.

2. Description of the Prior Art

Immunoglobulin G (IgG) preparations isolated from human blood plasma are effective in the treatment of various severe infectious diseases and immunological deficiency syndrome such as hypogammaglobulinemia and agammaglobulinemia. The widely used method for isolating IgG from human blood plasma is Cohn's plasma protein fractionation method.

In Cohn's plasma protein fractionation method, IgG is obtained from Cohn fraction II or II+III. However, the recovered IgG may contain a significant amount of aggregates because IgG tends to aggregate spontaneously during storage of human blood plasma or tends to aggregate in contact with alcohol or other chemicals during the fractionation procedure, or also tends to aggregate during lyophilization. If IgG containing aggregates is administered intravenously, the aggregates may exert an anticomplement effect to cause serious anaphylactoid reactions such as hypotension, chill and fever.

Accordingly, IgG preparations for use in intravenous injection require that no aggregates are detectable when they are analyzed by the gel filtration method using a suitable carrier and that their anticomplementary activity is not greater than 20 units when determined at an IgG concentration of 5%. The term "aggregate" as used herein means any cluster formed by the combination of a plurality of IgG molecules, but does not include the dimer of IgG. It is desirable that, in addition to meeting the above requirement, the anticomplement activity is as low as possible. Thus, in order to obtain an IgG preparation for use in intravenous injection, it is necessary to remove aggregates from IgG isolated from Cohn fraction II or II+III. The methods which can be used for this purpose include:

(1) the polyethylene glycol precipitation method (i.e., the method in which polyethylene glycol is added to an aqueous IgG solution containing aggregates and the resulting precipitate of aggregates is separated by filtration);

(2) the method of dissociating aggregates by reducing the pH of an aggregate-containing aqueous IgG solution to a low value such as 4 (i.e., the method in which an aqueous IgG solution is adjusted to a pH of about 4 by the addition of an acid, allowed to stand for a certain time so as to dissociate the aggregates, and then neutralized);

(3) A combination of the method described in paragraph (2) above and the method of decomposing aggregates by means of a slight amount of a proteolytic enzyme (i.e., the method in which an aqueous solution of IgG is adjusted to pH about 4 and a slight amount of a proteolytic enzyme such as pepsin is added thereto so as to effect both the dissociation of aggregates by the acid and the decomposition of aggregates by the enzyme, followed by neutralization of the aqueous solution and removal of the enzyme by adsorption to an ion exchange resin);

(4) the method of removing aggregates by adsorption to an ion exchange resin;

(5) the method of removing aggregates by adsorption to an adsorbent such as tricalcium phosphate, activated charcoal, aluminum hydroxide or bentonite (i.e., the method in which such an adsorbent is added to an aqueous solution of IgG so as to cause aggregates to be adsorbed thereto, and the adsorbent is then separated by filtration);

(6) the gel filtration method (i.e., the method in which aggregates are separated and removed by gel chromatography using a gel filtering medium, such as Sephadex G-200, having a fractionating molecular weight capable of separating aggregates from IgG monomer);

(7) the membrane separation method;

and the like.

As an example of the membrane separation method, there has been proposed a filtration method using a porous polymethyl methacrylate membrane which permits the passage of IgG monomer and dimer but blocks the passage of aggregates (Japanese Patent Laid-Open No. 69732/'86). Moreover, it is also known to remove aggregates by filtration through a polycarbonate membrane filter having a pore diameter of 0.05 to 0.2 μm (Japanese Patent LaidOpen No. 167518/'83).

Generally, IgG (monomer) has a size of about 10 nm, IgG dimer usually contained in an aqueous solution of IgG has a size of about 12 nm, and aggregates predominantly have a size of about 14 nm and more. Thus, they are similar in size. For this reason, the abovedescribed polyethylene glycol precipitation method, the adsorption method (using an ion exchange resin, activated charcoal, tricalcium phosphate or the like) and the gel filtration method have been disadvantageous in that, even if aggregates are removed to such an extent that they are not directly detectable by gel filtration analysis, the anticomplementary activity believed to be attributable mainly to aggregates cannot be reduced satisfactorily. This means that the aggregates have not been removed to a full extent. In contrast, the membrane separation method makes it possible to remove aggregates completely and thereby reduce the anticomplementary activity satisfactorily. However, since the size of IgG monomer and dimer (hereinafter referred to collectively as IgG) is close to that of aggregates, the membrane separation method also has the disadvantage that, if it is tried to remove aggregates completely, the recovery of IgG and the treating efficiency become too low to be practicable. On the other hand, if a membrane having a relatively large pore size is used to enhance the treating efficiency, it is difficult to remove aggregates to such an extent that the anticomplementary activity is reduced satisfactorily. Moreover, the membrane separation method also has the disadvantage that IgG tends to aggregate again at the interface between the membrane and the solution and, therefore, the resulting filtrate has a high anticomplementary activity.

Thus, it has been difficult to efficiently remove aggregates from an aqueous solution of IgG according to any one of conventionally known methods and thereby reduce its anticomplement activity to less than 10 units (at an IgG concentration of 5%). Accordingly, it would be desirable to develop a method which can remove aggregates to such a degree that they are not directly detectable and thereby produce an aqueous solution of IgG having a greatly reduced anticomplementary activity and capable of being adjusted to any desired concentration.

SUMMARY OF THE INVENTION

In view of these circumstances, the present inventors have made an intensive study and have discovered that, by treating an aqueous solution of crude IgG according to a conventional technique to remove aggregates therefrom to such an extent that they are not detectable by gel filtration analysis, and then filtering the resulting IgG solution (or stock solution) through a porous polyolefin membrane in the presence of a stabilizer having surface activity, the anticomplementary activity can be greatly reduced without causing any substantial reaggregation of IgG by the filtration. The present invention has been completed on the basis of this discovery.

Thus, the present invention provides a process for the production of immunoglobulin G which comprises providing an aqueous solution of immunoglobulin G isolated from human blood plasma, removing aggregates from the aqueous solution of immunoglobulin G to such an extent that they are not detectable by gel filtration analysis, and filtering the aqueous solution of immunoglobulin G through a porous polyolefin membrane in the presence of a stabilizer having surface activity. The aqueous solution of IgG thus obtained or its freezedried product is suitable for use in intravenous injection.

According to the present invention, in spite of the fact that the porous membrane used had a pore diameter which is essentially incapable of rejecting IgG aggregates, the aggregates can be efficiently removed to obtain an aqueous solution of IgG having a greatly reduced anticomplementary activity, without causing any reaggregation of IgG by the filtration. Moreover, since the pore size of the porous membrane is relatively large, the process of the present invention does not suffer from a reduction in IgG recovery or treating efficiency.

DETAILED DESCRIPTION AND THE PREFERRED EMBODIMENTS

Figure 1:
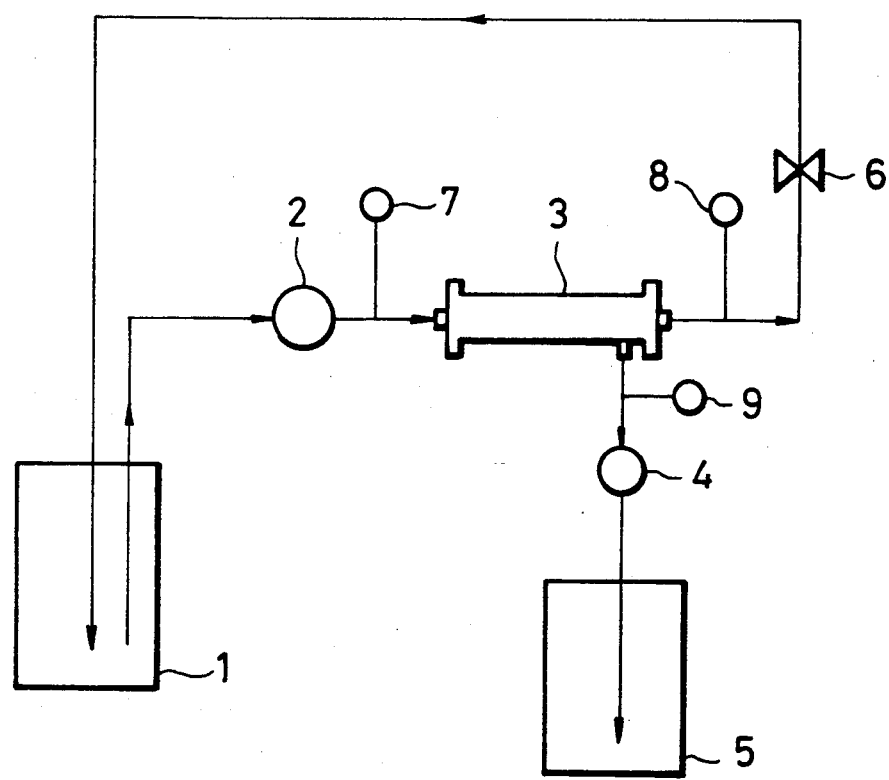
FIG. 1 is a flow diagram illustrating a membrane filtration apparatus used in the examples of the present invention.

In the following description, for the sake of convenience, an IgG-containing material obtained from Cohn fraction II or II+III is referred to as "crude IgG", an IgG-containing solution preliminarily purified to such as extent that aggregates are not detectable is referred to as "an IgG stock solution", and an IgG-containing solution obtained by filtering an IgG stock solution through a porous polyolefin membrane is referred to as "an IgG filtrate".

The crude IgG used in the process of the present invention can be recovered according to any of conventional techniques including Cohn's plasma protein fractionation method. However, it is common practice to employ Cohn's plasma protein fractionation method. Although both a pastelike material obtained as Cohn fraction II or II+III and a freeze-dried product of Cohn fraction II or II+III can be used, it is preferable to use a pastelike material because the amount of aggregates is increased by freeze drying. In carrying out the process of the present invention, crude IgG is dissolved in distilled water, physiological saline or a buffer solution having a pH of about 4 to 9. Then, the resulting solution is subjected to the following treatment.

In the process of the present invention, an aqueous solution of crude IgG is first freed of aggregates to such an extent that they are not detectable by gel filtration analysis. The term "gel filtration analysis" as used herein means an analysis by aqueous size-exclusion chromatography having accuracy enhanced by use of a hard gel with a particle diameter of about 10 $\mu$m. Typically, this analysis is carried out by using a TSK-G3000 SW column manufactured by Tosoh Co., Ltd. The methods which can be employed for this purpose include, for example, the polyethylene glycol precipitation method, the method of adsorption by an ion exchange resin, the method of adsorption by tricalcium phosphate, activated charcoal, aluminum hydroxide, bentonite or the like, the gel filtration method, the low-pH treatment method, and the method comprising a combination of low-pH treatment and proteolytic enzyme treatment. Moreover, any other method that can remove aggregates to an undetectable extent may also be employed. However, no matter which method is employed, it is difficult to reduce the anticomplementary activity of the resulting aqueous solution of IgG to less than 10 units at an IgG concentration of 5%. Usually, the resulting aqueous solution of IgG has an anticomplementary activity of about 10 to 30 units. The anticomplementary activity shown herein refers to a value measured by the method of Kabat and Mayer [Mayer, M. M.: Experimental Immunochemistry (ed. by Kabat, E. A., and Mayer, M. M.), 2nd. edition, pp. 133-240 (1961)]. Among the above-described methods for the removal of aggregates, the method of adsorption by tricalcium phosphate is preferred.

By way of example, the method of adsorption by tricalcium phosphate may be carried out by adding tricalcium phosphate powder to a solution to be treated in an amount of 2% by weight based on the weight of the solution, stirring this mixture to cause aggregates to be adsorbed to the tricalcium phosphate, and then separating the tricalcium phosphate by filtration.

In the process of the present invention, the IgG stock solution from which aggregates have been removed in the above-described manner is then filtered through a porous polyolefin membrane in the presence of a stabilizer having surface activity, whereby its anticomplementary activity can be greatly reduced without causing any appreciable reaggregation of IgG.

From the viewpoint of membrane separation efficiency, the IgG stock solution filtered through a polyolefin membrane should preferably have an IgG concentration of 1 to 10% by weight. If necessary, therefore, the IgG concentration of the IgG stock solution is adjusted in advance by dilution with distilled water or physiological saline, or by concentration through ultrafiltration or other suitable technique. It is essential that a stabilizer having surface activity be added to the stock solution. The stabilizer used in the present invention has the function of preventing the aggregation of IgG and exhibits marked adsorption to solid-liquid interfaces. Useful stabilizers includes, for example, protein type polymers of plant origin, animal origin such as human serum albumin, Cohn fraction V and gelatin derivatives (e.g., polyoxygelatin, decomposed/succinylated gelatin and decomposed/urea-crosslinked gelatin), and polymeric nonionic surfactants such as polyvinyl pyrrolidone, polyethylene glycol and oxyethyleneoxypropylene block copolymers. These stabilizers may be used alone or in admixture of two or more. Although the amount of stabilizer used may vary according to the type thereof, it is preferably used in an amount of 0.01 to 1 part by weight per part by weight of the IgG present in the IgG stock solution. Too small amounts of stabilizer will produce no effect, while too large amounts will bring about no further improvement in effect.

If an IgG stock solution containing no stabilizer is subjected to a membrane filtration, IgG tends to aggregate irrespective of the type of membrane used, so that it is difficult to reduce its anticomplementary activity. Even in the presence of stabilizer, filtration of an IgG stock solution by using membranes except those made of polyolefin also tends to cause the aggregation of IgG. In contrast, the process of the present invention can prevent the aggregation of IgG during membrane filtration and can reduce the anticomplementary activity efficiently. The reason for this has not been clarified yet, but it is believed to be that the stabilizer having surface activity is preferentially adsorbed to the hydrophobic surface of the polyolefin membrane and, therefore, the IgG being filtered is protected from aggregation.

The polyolefin membranes which can be used in the process of the present invention include, for example, those formed of such materials as polyethylene, polypropylene and poly-4-methylpentene-1. Useful polyolefin membranes are porous ones, and the pore diameter thereof may be such that, when an aqueous solution of crude IgG containing aggregates is filtered and the resulting filtrate is analyzed by the gel filtration method, aggregates are detectable therein. Rather, membranes having such a large pore diameter are preferred because they can provide a high flux and a high recovery of IgG. Thus, in spite of the fact that the membrane used has a geometrical pore size larger than the size of aggregates, the process of the present invention makes it possible to capture aggregates efficiently and reduce the anticomplementary activity attributable thereto. Specifically, the pore diameter of the membrane, as measured by the standard particle filtration method, is preferably within the range of 0.015 to 0.17 $\mu$m, more preferably within the range of 0.018 to 0.10 $\mu$m, and most preferably within the range of 0.02 to 0.06 $\mu$m. If the pore diameter is less than the lower limit of the above range, the filtration rate tends to become lower and, therefore, the treating efficiency tends to be reduced. In particular, membranes which substantially reject aggregates are not suitable for practical purposes because they provide a low recovery of IgG and a low filtration efficiency. Even if the pore diameter is greater than the upper limit of the above range, no serious problem arises, but the degree of reduction of the anticomplementary activity of the resulting filtrate tends to decrease. The reason why anticomplementary activity can be effectively decreased by a membrane having a geometrical pore size larger than the size of aggregates is unknown. It is possible to speculate that the anticomplementary activity is partially due to the presence of slight amount of aggregates which may be too small to be detected by gel filtration analysis and too large to pass through said membrane. Judging from the fact that the presence of a stabilizer having surface activity is indispensable, the interfacial adsorptivity of the stabilizer is also believed to take part in the capture of aggregates.

Examples of such polyolefin membranes include polyethylene hollow-fiber membranes EHF® 390A, EHF® 390C and EHF® 270H that are manufactured by Mitsubishi Rayon Co., Ltd. These membranes, which have been made porous by stretching, are preferred in that they do not contain any additive used to make them porous.

Since polyolefin membranes are naturally hydrophobic, it is difficult to allow an aqueous solution to pass through a polyolefin membrane used as such. In filtering an aqueous solution, it is preferable to use a polyolefin membrane which has been subjected to some treatment for hydrophilization. For use in the process of the present invention, porous polyolefin membranes whose surface are not chemically modified (i.e., polyolefin membranes which have not undergone the so-called permanent hydrophilization) are preferred because they can effectively prevent the interfacial aggregation of IgG during membrane separation procedure. Polyolefin membranes which have undergone non-permanent hydrophilization include, for example, one which has been treated by wetting the inner wall of the pores with a water-miscible organic solvent such as alcohol and then replacing it with water to make the membrane capable of filtering aqueous solutions, and one which has been treated by physically attaching a surface-active stabilizer as described above to the inner wall of the pores to make the membrane capable of water filtration.

If a membrane as described above is used, the anticomplementary activity can be substantially reduced by causing the coexistent stabilizer having surface activity to be efficiently adsorbed to the membrane surface and suppressing the interfacial aggregation of IgG at the membrane surface.

The membrane may be in the form of a flat film or a tubular film. However, a hollow-fiber membrane is preferred because it permits a compact apparatus to be fabricated.

Preferably, the membrane filtration is of the cross flow type.

FIG. 1 is a flow diagram illustrating an exemplary apparatus which can be used for purposes of membrane filtration in the process of the present invention. Specifically, an IgG stock solution is introduced from an IgG stock solution tank 1 into a membrane filtration module 3 by means of a feed pump 2. The resulting filtrate is collected by means of a suction pump 4 and recovered in a filtrate tank 5. The pressures at the inlet and outlets of module 3 are measured with pressure gauges 7, 8 and 9 and controlled by means of a pressure regulating valve 6. Where a hollow-fiber membrane is used, it is desirable to circulate a solution to be treated over the membrane surface preferably at a linear speed of 0.1 to 10 cm/sec and filtering it at a transmembrane pressure of 300 mmHg or less and preferably 150 mmHg or less. In a filtration of the cross flow type, the concentration of the IgG stock solution may become higher as the treatment proceeds. In such a case, appropriate amounts of solvent can be added to the IgG stock solution so as to adjust the IgG concentration properly and thereby maintain a high recovery of IgG.

The operating temperature for the membrane filtration is usually in the range of 2° to 37° C. and preferably in the range of 4° to 20° C.

If necessary, the IgG stock solution is subjected to the membrane filtration after its IgG concentration has been properly adjusted to a desired level by dilution with distilled water or physiological saline or by concentration through ultrafiltration. The aqueous solution of IgG thus obtained can also be freeze-dried for use in intravenous injection as necessary.

The present invention is further illustrated by the following examples.

In these examples, anticomplementary activity was determined by the method of Kabat and Mayer described above.

EXAMPLE 1

One part by weight of Cohn fraction II in paste form was dissolved in 4 parts by weight of distilled water. Then, tricalcium phosphate was added thereto in an amount of 2% by weight based on the distilled water. This mixture was stirred for 12 hours to cause aggregates to be adsorbed to the tricalcium phosphate, and then filtered to obtain a solution. In this solution, no aggregates were detectable by gel filtration analysis. To this solution was added a decomposed and ureacrosslinked gelatin derivative (commercially available from Hoechst AG under the trade name of Heamaccel ® as a stabilizer in an amount of 0.5 part by weight per part by weight of IgG. Thereafter, the solution was concentrated by ultrafiltration to an IgG concentration of 5.5%. Thus, there was obtained 400 ml of an IgG-/Heamaccel ® mixed solution, which was used as an IgG stock solution (hereinafter referred to briefly as the stock solution).

A module having a membrane area of 0.6 m² was fabricated by using, as a porous polyolefin membrane, the porous polyethylene hollow-fiber membrane HEF ® 390C (manufactured by Mitsubishi Rayon Co., Ltd. and having an average pore size of 0.03 μm as measured by the standard particle filtration method). This module was temporarily hydrophilized by impregnating the membrane with ethanol and then substituting water for the ethanol. Thereafter, this module was incorporated into an apparatus having a flow path as illustrated in FIG. 1. Using this apparatus, the stock solution was filtered under conditions including an operating temperature of 6° C., a transmembrane pressure of 100 mmHg (as controlled with a pressure regulating valve 6), and a stock solution feed rate of 200 ml/min., so that 300 ml of filtrate was recovered. The IgG concentration of the filtrate was 3.1%, the apparent permeability was 55%, and the IgG recovery was 42%. The anticomplementary activity of the stock solution adjusted to an IgG concentration of 2.5% was 10 units, whereas that of the filtrate having the same IgG concentration was 1 unit. The ratio of the anticomplementary activity after filtration to that before filtration was 0.1.

EXAMPLE 2

The procedure of Example 1 was repeated except that there was used a filtration module (having the same membrane area) fabricated by using, as the porous polyethylene hollow-fiber membrane, EHF ® 390A (having an average pore diameter of 0.02 μm as measured by the standard particle filtration method) in place of EHF ® 390C.

The IgG concentration of the filtrate was 2.8%, the apparent permeability was 50%, and the IgG recovery was 27%. The anticomplementary activity of the filtrate was 3 units at an IgG concentration of 2.5%, and the ratio of the anticomplementary activity after filtration to that before filtration was 0.3.

EXAMPLE 3

One part by weight of Cohn fraction II in paste form was dissolved in 4 parts by weight of distilled water. Then, tricalcium phosphate was added thereto in an amount of 2% by weight based on the distilled water. This mixture was stirred for 12 hours to cause aggregates to be adsorbed to the tricalcium phosphate, and then filtered to obtain a solution. To this solution was added Heamaccel ® as a stabilizer in an amount of 0.4 part by weight per part by weight of IgG. Thereafter, the solution was concentrated by ultrafiltration to obtain 2,800 ml of an IgG/Heamaccel ® mixed solution having an IgG concentration of 6%.

Using the same hollow-fiber membrane module as used in Example 1, the above stock solution was circulated through a flow path as illustrated in FIG. 1 and filtered in a constant-rate filtration process using a pump 4. At a stock solution feed rate of 200 ml/min. and a filtrate flow rate of 10 ml/min., 2100 ml of filtrate was recovered. During filtration, the transmembrane pressure was within the range of 80 to 120 mmHg.

The IgG concentration of the filtrate was 5.1%, the apparent permeability was 86%, and the IgG recovery was 64%. When the anticomplementary activities of the stock solution and the filtrate were measured at an IgG concentration of 4%, the stock solution had an anticomplementary activity of 11 units and the filtrate had an anticomplementary activity of 4 units. The ratio of the anticomplementary activity after filtration to that before filtration was 0.36.

EXAMPLE 4

The procedure of Example 3 was repeated except that the concentration by ultrafiltration was carried out until an IgG concentration of 5% was attained. Thus, there was obtained 2,800 ml of an IgG/Heamaccel ® mixed solution.

Using the same hollow-fiber membrane module as used in Example 1, the above stock solution was circulated through a flow path as illustrated in FIG. 1 and filtrated in a constant-rate filtration process using a pump 4. Using a stock solution feed rate of 200 ml/min. and a flux of 12 ml/min., the stock solution was filtered with a 150 mM aqueous solution of sodium chloride continuously added thereto at a rate of 4.8 ml/min. During filtration, the transmembrane pressure was within the range of 80 to 120 mmHg.

Since the volume of the stock solution became very small, the filtration was stopped at the time when 4600 ml of filtrate was recovered.

The IgG concentration of the filtrate was 3%, the apparent permeability was 64%, and the IgG recovery was 99%. When the anticomplementary activities of the stock solution and the filtrate were measured at an IgG concentration of 4%, the stock solution had an anticomplementary activity of 11 units and the filtrate had an anticomplementary activity of 3 units. The ratio of the anticomplementary activity after filtration to that before filtration was 0.27.

EXAMPLE 5

One part by weight of Cohn fraction II in paste form was dissolved in 5 parts by weight of distilled water. Then, tricalcium phosphate was added thereto in an amount of 2% by weight based on the distilled water. This mixture was stirred for 12 hours to cause aggregates to be adsorbed to the tricalcium phosphate, and then filtered to obtain a solution. To this solution was added human serum albumin as a stabilizer in an amount of 0.08 part by weight per part by weight of IgG. Thereafter, the solution was concentrated by ultrafiltration to obtain 2,800 ml of an IgG/albumin mixed solution having an IgG concentration of 6%.

In the same manner as described in Example 4, the above stock solution was filtered through the hollow-fiber membrane EHF ® 390C.

The IgG concentration of the filtration was 3%, the apparent permeability was 60%, and the IgG recovery was 98%. The anticomplementary activity of the stock solution adjusted to an IgG concentration of 2.5% was 9 units, whereas that of the filtrate having the same IgG concentration was 3 units. The ratio of the anti-complementary activity after filtration to that before filtration was 0.33.

COMPARATIVE EXAMPLE 1

Using a membrane filter having an average pore diameter of 0.1 μm (i.e., a nylon 66 membrane commercially available from Pall Corp. under the trade name of Seal Kleen ®), 270 ml of the same IgG/Heamaccel ® mixed solution (having an IgG concentration of 6%) as used in Example 3 was filtered at a treating temperature of 5°–6° C. and an inlet pressure of 0.5 kg/cm$^2$. The IgG concentration of the filtrate was 5.8%, the apparent permeability was 96%, and the IgG recovery was 71%. When the stock solution and the filtrate were adjusted to an IgG concentration of 4% and their anticomplementary activities were measured, the stock solution had an anticomplementary activity of 11 units and the filtrate had an anti-complementary activity of 8 units. The ratio of the anti-complementary activity after filtration to that before filtration was 0.73, indicating that no substantial reduction in anticomplementary activity was caused by the filtration.

COMPARATIVE EXAMPLE 2

The procedure of Comparative Example 1 was repeated except that the same IgG/Heamaccel ® mixed solution (having an IgG concentration of 5%) as used in Example 4 was filtered at an inlet pressure of 0.3 kg/cm$^2$. The IgG concentration of the filtrate was 5%. When the anticomplementary activities of the stock solution and the filtrate were measured at an IgG concentration of 4%, the stock solution had an anticomplementary activity of 11 units and the filtrate had an anti-complementary activity of 7 units. The ratio of the anticomplementary activity after filtration to that before filtration was 0.64.

COMPARATIVE EXAMPLE 3

An IgG/Heamaccel ® mixed solution was obtained in the same manner as described in Example 1, except that its IgG concentration was adjusted to 5.7%. On the other hand, an ultrafiltration module (having a membrane area of 0.6 m$^2$) was fabricated by using a flat ultrafiltration membrane formed of polyether sulfone (Omega ® 1000K manufactured by Filtron Corp. and having a fractionating molecular weight of 1,000,000). Using this module, 760 ml of the above stock solution was filtered at a filtering temperature of 15° C. and a stock solution feed rate of 190 ml/min. The IgG concentration of the filtrate was 5.6%, the apparent permeability was 98%, and the IgG recovery was 86%. When the anticomplementary activities of the stock solution and the filtrate were measured at an IgG concentration of 5%, the stock solution had an anticomplementary activity of 20 units and the filtrate had an antiocomplementary activity of 19 units. The ratio of the anticomplementary activity after filtration to that before filtration was 0.95.

COMPARATIVE EXAMPLE 4

An ultrafiltration module (having a membrane area of 0.07 m$^2$) was fabricated by using a flat ultra-filtration membrane formed of polyether sulfone (Omega ® 300K manufactured by Filtron Corp. and having a fractionating molecular weight of 300,000). Using this module, 760 ml of the same IgG/Heamaccel ® mixed solution as used in Example 3 was filtered at a filtering temperature of 15° C. and a stock solution feed rate of 190 ml/min. The IgG concentration of the filtrate was 2.7%, the apparent permeability was 98%, and the IgG recovery was 80%. When the anticomplementary activities of the stock solution and the filtrate were measured at an IgG concentration of 2.5%, the stock solution had an anticomplementary activity of 10 units and the filtrate had an anticomplementary activity of 6 units. The ratio of the anticomplementary activity after filtration to that before filtration was 0.6.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A process for production and filtering of immunoglobulin G which comprises providing an aqueous solution of immunoglobulin G isolated from human blood plasma, removing aggregates from the aqueous solution of immunoglobulin G to such an extent that they are not detectable by gel filtration analysis, and filtering the aqueous solution of immunoglobulin G through a porous polyolefin membrane having a pore diameter in the range of 0.015 to 0.17 microns in the presence of an added surface active stabilizer.

2. A process as claimed in claim 1, wherein the surface active stabilizer is selected from the group consisting of human serus albumin, and Cohn fraction V.

3. A process as claimed in claim 1, wherein the surface active stabilizer is a gelatin derivative.

4. A process as claimed in claim 3, wherein said gelatin derivative is selected from the group consisting of polyoxygelatin, decomposed/succinylated gelatin and decomposed/urea-crosslinked gelatin.

5. A process as claimed in claim 1, wherein the surface active stabilizer is a polymeric nonionic surfactant.

6. A process as claimed in claim 5, wherein said polymeric nonionic surfactant is selected from the group consisting of polyvinyl pyrrolidone, polyethylene glycol and oxyethylene-oxypropylene block copolymers.

7. A process as claimed in claim 1, wherein said surface active stabilizer is present in an amount of 0.01 to 1 part by weight per part by weight of immunoglobulin G.

8. A process as claimed in claim 1, wherein said membrane has a pore size in the range of 0.018 to 0.10 microns.

9. A process as claimed in claim 1, wherein said membrane has a pore size in the range of 0.02 to 0.06 microns.

* * * * *